United States Patent
Aoun

(10) Patent No.: US 10,619,333 B1
(45) Date of Patent: Apr. 14, 2020

(54) METHODS, SYSTEMS TO FACILITATE ATMOSPHERIC WATER GENERATION, AND REGULATION OF AN ENVIRONMENT OF ATMOSPHERIC WATER GENERATION

(71) Applicant: Joseph Aoun, New York, NY (US)

(72) Inventor: Joseph Aoun, New York, NY (US)

( * ) Notice: Subject to any disclaimer, the term of this patent is extended or adjusted under 35 U.S.C. 154(b) by 0 days.

(21) Appl. No.: 16/545,271

(22) Filed: Aug. 20, 2019

Related U.S. Application Data

(62) Division of application No. 16/248,494, filed on Jan. 15, 2019.

(60) Provisional application No. 62/743,274, filed on Oct. 9, 2018.

(51) Int. Cl.
| | |
|---|---|
| *E03B 3/28* | (2006.01) |
| *B01D 53/26* | (2006.01) |
| *B01D 46/44* | (2006.01) |
| *C02F 1/00* | (2006.01) |
| *B01D 5/00* | (2006.01) |
| *A61L 9/20* | (2006.01) |

(52) U.S. Cl.
CPC .............. *E03B 3/28* (2013.01); *A61L 9/20* (2013.01); *B01D 5/009* (2013.01); *B01D 5/0051* (2013.01); *B01D 5/0072* (2013.01); *B01D 46/444* (2013.01); *B01D 53/265* (2013.01); *C02F 1/004* (2013.01); *C02F 1/008* (2013.01); *A61L 2209/111* (2013.01)

(58) Field of Classification Search
None
See application file for complete search history.

(56) References Cited

U.S. PATENT DOCUMENTS

| | | | | |
|---|---|---|---|---|
| 2013/0047655 | A1* | 2/2013 | White | B01D 5/0006 62/264 |
| 2016/0129369 | A1* | 5/2016 | Dorfman | B01D 5/0051 |
| 2016/0212948 | A1* | 7/2016 | McGuire | A01G 9/247 |
| 2017/0189597 | A1* | 7/2017 | Caluya | A61M 1/16 |
| 2018/0332830 | A1* | 11/2018 | Gordon | C02F 1/441 |

\* cited by examiner

*Primary Examiner* — Christopher P Jones
*Assistant Examiner* — Phillip Y Shao

(57) ABSTRACT

A method of facilitating atmospheric water generation is disclosed. The method may include receiving, using a communication device, sensor data from at least one sensor associated with an Atmospheric Water Generator (AWG). Further, the at least one sensor may be configured for sensing at least one characteristic of an environment of the AWG. Further, the method may include analyzing, using a processing device, the sensor data. Further, the method may include determining, using the processing device, a quality parameter associated with the environment based on the analyzing. Further, the method may include generating, using the communication device, at least one operational parameter based on the quality parameter. Further, the method may include and transmitting, using the communication device, the at least one operational parameter to at least one regulator configured for controlling the at least one characteristic of the environment based on the at least one operational parameter.

6 Claims, 12 Drawing Sheets

METHODS, SYSTEMS TO FACILITATE ATMOSPHERIC WATER GENERATION, AND REGULATION OF AN ENVIRONMENT OF ATMOSPHERIC WATER GENERATION

The current application is a Divisional application of a U.S. non-provisional application Ser. No. 16/248,494 filed on Jan. 15, 2019. The U.S. non-provisional application Ser. No. 16/248,494 claims a priority to a U.S. provisional application Ser. No. 62/743,274 filed on Oct. 9, 2018.

FIELD OF THE INVENTION

The present disclosure relates generally to the field of data processing. More specifically, the present disclosure describes methods and systems to facilitate atmospheric water generation, and regulation of an environment of atmospheric water generation.

BACKGROUND OF THE INVENTION

Atmospheric water generators, which include pumping air a machine condensation area of an atmospheric water generator, Water exposure to ultraviolet light to remove bacteria and microorganisms, and water filtration by special filters to adjust water minerals content and remove impurities are widely used and well known.

Further, environmental conditions, such as quality of air available, relative percentage of humidity in air, etc., in which these atmospheric water generators are used vary with a change in location and geography. However, most atmospheric water generators are similar in design and in operation.

Further, no considerations of environmental conditions, such as quality of air available, relative percentage of humidity in air, etc. are taken generally while installation, and working of the atmospheric water generators.

Further, systems, which may manipulate environmental conditions, such as quality of air available, relative percentage of humidity in air, etc. and regulate these conditions to improve quality of water generated from the atmospheric water generators do not exist.

Further, systems, which may manipulate operational parameters of atmospheric water generators based on contextual parameters of atmospheric water generators installed in similar geographical, and environmental conditions do not exist.

Therefore, there is a need for improved methods and systems to facilitate atmospheric water generation, and regulation of an environment of atmospheric water generation that may overcome one or more of the above-mentioned problems and/or limitations.

SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a method of facilitating atmospheric water generation is disclosed. The method may include receiving, using a communication device, sensor data from at least one sensor associated with an Atmospheric Water Generator (AWG). Further, the at least one sensor may be configured for sensing at least one characteristic of an environment of the AWG. Further, the method may include analyzing, using a processing device, the sensor data. Further, the method may include determining, using the processing device, a quality parameter associated with the environment based on the analyzing. Further, the method may include generating, using the communication device, at least one operational parameter based on the quality parameter. Further, the method may include and transmitting, using the communication device, the at least one operational parameter to at least one regulator configured for controlling the at least one characteristic of the environment based on the at least one operational parameter. In some embodiments, the at least one characteristic of the environment may include a quantitative indication of one or more of temperature, pressure, humidity, pollutant and microorganism.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAIL DESCRIPTIONS OF THE INVENTION

Figure 1:
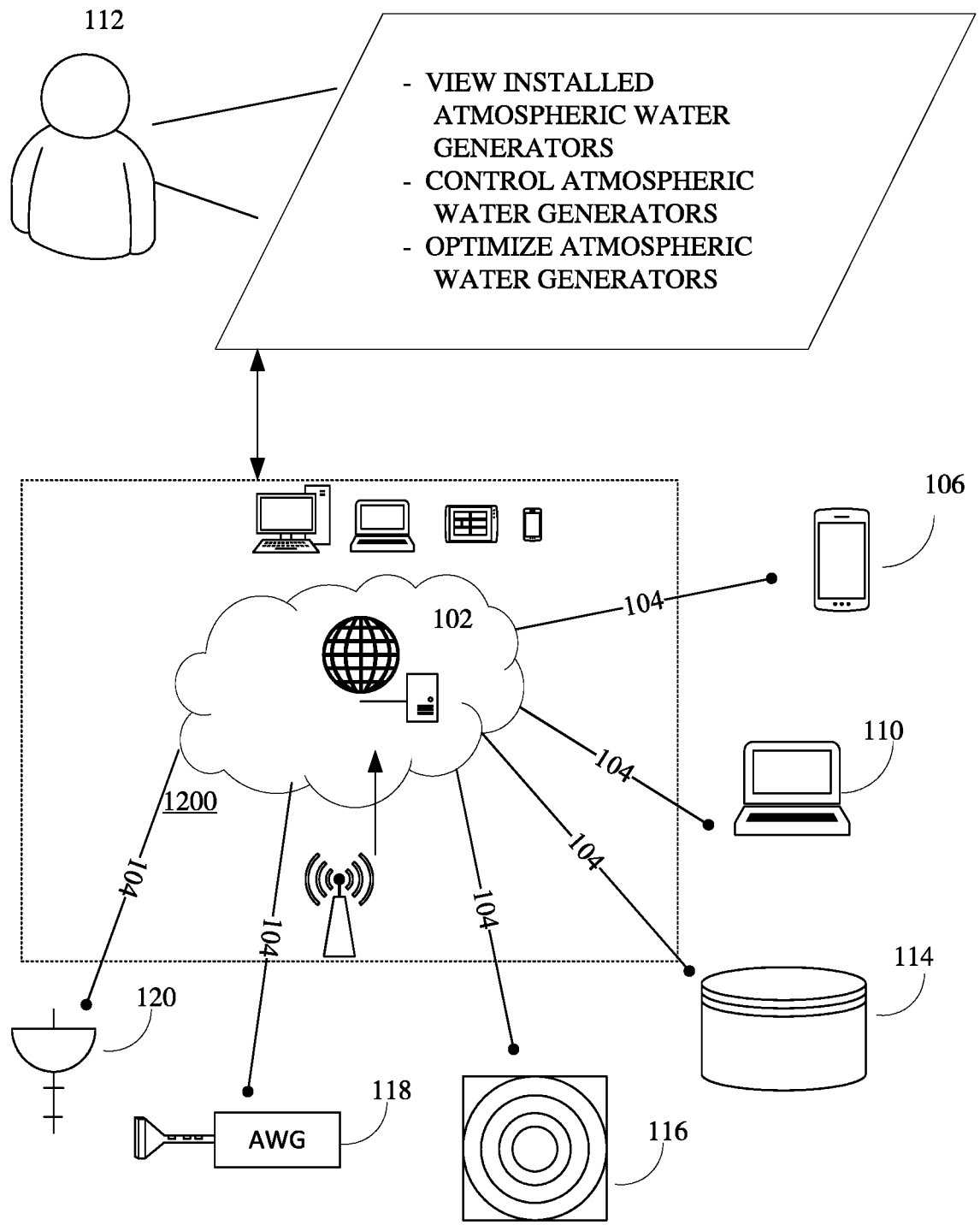
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of atmospheric water generation, and regulation of an environment of atmospheric water generation, embodiments of the present disclosure are not limited to use only in this context.

Overview:

Working of an AWG may include pumping air to a condensation area, exposing water received by condensation to ultraviolet light to remove bacteria and microorganisms, and water filtration by special filters that may adjust water minerals content and remove impurities. However, the input air may be contaminated with microorganisms and particulates, which may be passed to a water reservoir of the AWG. Further, the amount of mineral content in the water may be low or inconsistent by time.

Accordingly, to overcome the aforementioned problems, Input air quality may need to be maintained. Air quality may be managed by filtering input air that enters in an area/room/enclosure where the AWG machine may be located, and filtering and sterilizing air that may be pumped into the AWG. In the two stages of air filtration, filters used may not prevent humidity or have any anti-humidity property.

The area/room/enclosure where the AWG machine may be located may include filtered ventilation systems. For instance, Afpro® bag filters or similar filters may be used in an air conditioning system or air-flow system for the area/room/enclosure where the AWG machine may be located. Further, microorganism growth, such as bacterial or fungal may be impeded and may be made free of particles by use of HEPA air filters, and sterilization of the air with UV lights before the air reaches the condensation area of the AWG. The type of HEPA air filter, with a particular flow rate and resistance level, may be chosen on the basis of the AWG.

In summary, air may be controlled and filtered in two steps, first as the enters a room where the AWG may be placed, and second, before the air enters the condensation area in the AWG.

Further, the output air after filtration may be pumped out for recycling. Further, the air filtration process may have a positive effect on one or more water filtration units present in the AWG machine, increasing a life of the water filtration units due to a lack of dust or particulates entering the AWG.

Further, water filters may be used to control mineral content in water generated by the AWG. After water is generated, the water may pass through 4 stages of filtration, namely pre-carbon, post-carbon, reverse osmosis membrane, and TCR carbon.

Further, water production environment may need to be kept clean and free from airborne pathogens, in addition, the product (water) content of minerals and other chemicals should match standard laws and regulation in a region or country.

Further, chemical and biological tests may be performed from time to time according to rules and regulations to test the quality of the generated water. Water quality may need to be consistent each time and meet required standards. For instance, chemical tests for magnesium, calcium, sodium, potassium, chloride, bicarbonate, and sulfate may be performed.

FIG. 1 is an illustration of an online platform 100 consistent with various embodiments of the present disclosure. By way of non-limiting example, the online platform 100 to facilitate atmospheric water generation, and regulation of an environment of atmospheric water generation may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, sensors 116, an atmospheric water generator 118, and actuators 120 over a communication network 104, such as, but not limited to, the Internet. Further, users of the online platform 100 may include relevant parties such as, but not limited to, end users, water generation plant managers, and administrators. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 1200.

According to some embodiments, the online platform 100 may be configured to facilitate regulation of an environment and working of an atmospheric water generator (AWG). An atmospheric water generator (AWG) may extract water from humid ambient air by cooling the air below its dew point (condensation), and render the water potable.

Further, the online platform 100 may receive input from one or more sensors related to an environment of an Atmosphere Water Generator (AWG). For instance, the one or more sensors may include one or more air quality monitors. Accordingly, the one or more sensors may be configured to monitor parameters corresponding to the air quality of the environment of the AWG.

Further, the online platform 100 may analyze the received input to determine air quality in the environment of the AWG.

Further, the online platform 100 may transmit one or more operational parameters to one or more air filters to regulate the air quality in the environment of the AWG. The one or more operational parameters may describe and control the working of one or more air filtration machines, which may aid in the regulation of the quality of air in the environment of the AWG.

Further, the online platform 100 may receive contextual parameters related to one or more installations of one or more atmospheric water generators (AWGs). The one or more contextual parameters may include environmental parameters such as locations of the one or more installations, average temperature at the location during one or more times, and so on, technical specifications related to the one or more installations, and one or more operational parameters of the one or more AWGs, such as a time of operation, and additional details such as working of one or more components in the one or more AWGs, such as one or more air and/or water filters.

Further, the online platform 100 may analyze the contextual parameters related to one or more installations of the atmospheric water generators (AWGs). The analysis may include identifying a relationship between the one or more environmental parameters, technical specifications, and operational parameters included in the contextual parameters corresponding to the one or more AWGs.

Further, the online platform 100 may optimize one or more installations of atmospheric water generators (AWGs). For instance, based one or more on environmental factors of an installation of an AWG, the operational parameters of the AWG may be modified to optimize the generation of water from the AWG. Further, the online platform 100 may, through one or more actuators, control the working of the one or more AWGs based on the one or more modified operational parameters. In an instance, the AWGs may be placed in one or more special plants, to be protected from sun exposure, wind, sand, rain, cold weather and hot weather, which may also include along with and other safety measures such as but not limited to pest control by preventing rodents, insects, birds and animals and germs, air purification systems, and air isolation systems that may ensure that air inside the one or more special plants may be isolated from outside air.

Figure 2:
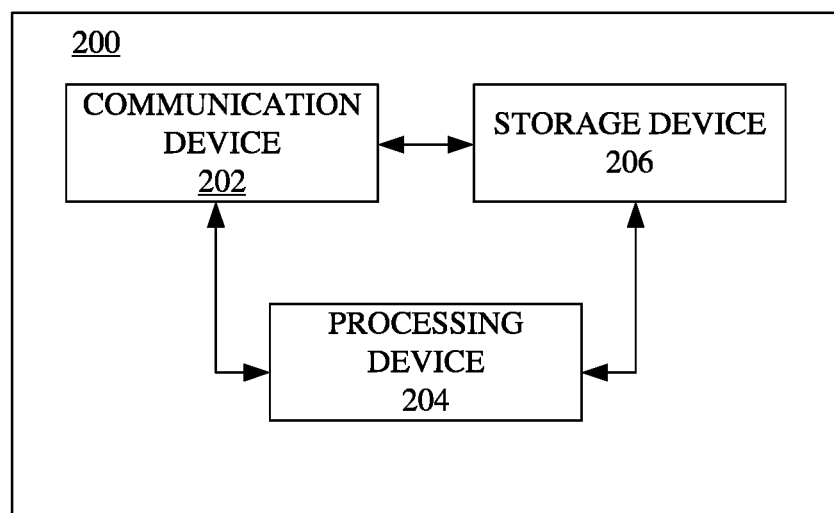
FIG. 2 shows a system for facilitating atmospheric water generation, in accordance with some embodiments.

FIG. 2 shows a system 200 for facilitating atmospheric water generation, in accordance with some embodiments. Accordingly, the system 200 may include a communication device 202 configured for receiving sensor data from at least one sensor associated with an Atmospheric Water Generator (AWG). Further, in some embodiments, the at least one sensor may be configured for sensing an environment (i.e. surrounding atmosphere) of the AWG. In some embodiments, the at least one sensor may be configured for sensing an interior region of the AWG. In some embodiments, the at least one sensor may be configured for sensing an operational state of at least one component of the AWG. In some embodiments, the at least one sensor may be configured for sensing a characteristic of at least one of an input substance (e.g. air), an intermediate substance and an output substance (e.g. water, by-products etc.) of the AWG. Further, the at least one sensor may be configured for sensing at least one characteristic of an environment of the AWG. Further, in some embodiments, the AWG may include a water filter configured for filtering water generated by the AWG. Further, the water filter may be configured for controlling mineral content of the water. Further, the at least one characteristic corresponds to the water. Further, in some embodiments, the at least one sensor may be configured for sensing one or more of a chemical substance and a biological substance in the water.

Further, the communication device 202 may be configured for transmitting at least one operational parameter to at least one regulator configured for controlling the at least one characteristic of the environment based on the at least one operational parameter. Further, in some embodiments, the at least one regulator may include an environment regulator, an input air regulator, a condensation region regulator, a water output regulator and so on. Further, in some embodiments, the at least one regulator may include at least one air filter configured for filtering air of the environment. Further, the at least one air filter may include a High efficiency particulate air (HEPA) filter. Further, in some embodiments, the at least one operational parameter corresponds to a flow rate and a resistance level associated with the HEPA filter. Further, in some embodiments, the at least one characteristic of the environment may include a quantitative indication of one or more of temperature, pressure, humidity, pollutant and microorganism. Further, in some embodiments, the at least one regulator may include an Ultra-Violet (UV) emitter configured for emitting UV radiation into the environment in order to sterilize the environment. Further, in some embodiments, the environment may include an air surrounding the AWG. Further, the AWG may include a condensation region in fluid communication with the air. Further, the UV emitter may be configured for emitting UV radiation into one or more of the air surrounding the AWG and the condensation region. Further, in some embodiments, the at least one operational parameter corresponds to the water filter.

Further, the system 200 may include a processing device 204 configured for analyzing the sensor data. Further, the processing device 204 may be configured for determining a quality parameter associated with the environment based on the analyzing. Further, the processing device 204 may be configured for generating the at least one operational parameter based on the quality parameter.

In further embodiments, the communication device 202 may be configured for receiving a plurality of contextual parameters associated with a plurality of installations of Atmospheric Water generators (AWGs). Further, the communication device 202 may be configured for transmitting at least one optimum operational parameter to an installation of the plurality of installations including an AWG. Further, the installation of at least one AWG regulator configured for controlling operation of the AWG may be based on the at least one optimum operational parameter. Further, the processing device 204 may be configured for analyzing the plurality of contextual parameters. Further, the processing device 204 may be configured for generating the at least one optimum operational parameter based on the analyzing of the plurality of contextual parameters. Further, the system 200 may include a storage device 206 configured for storing the at least one optimum operational parameter in association with indication of corresponding plurality of contextual parameters. Further, in some embodiments, the plurality of contextual parameters associated with the AWG may include a location data corresponding to a location of the AWG. Further, the system 200 may include retrieving, using the storage device 206, regulation data associated with operation of AWGs based on the location data. Further, the generating of the at least one optimum parameter may be further based on the regulation data.

Figure 3:
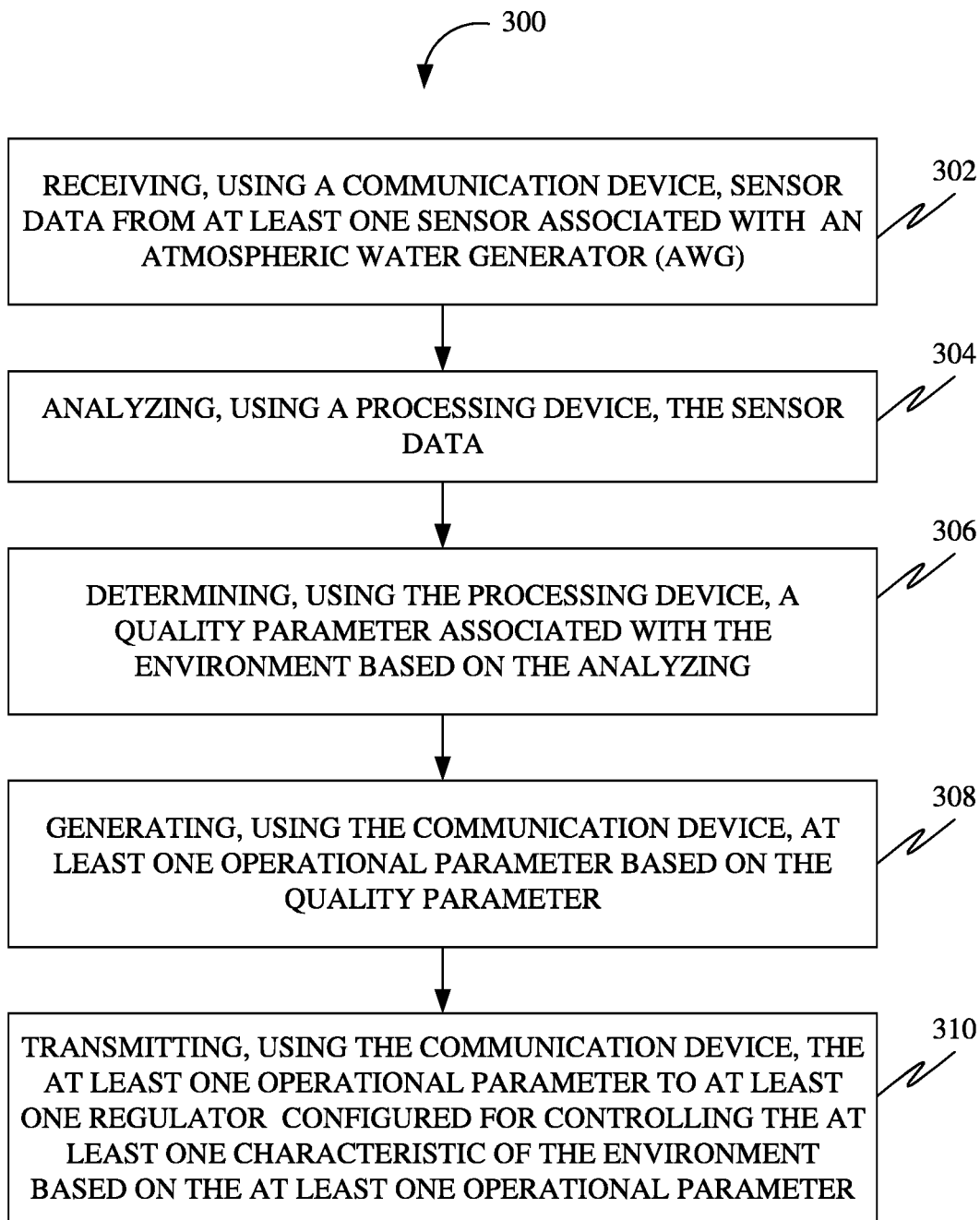
FIG. 3 is a flowchart of a method to facilitate atmospheric water generation, in accordance with some embodiments.

FIG. 3 is a flowchart of a method 300 to facilitate atmospheric water generation, in accordance with some embodiments. Accordingly, at 302, the method 300 may include receiving, using a communication device, sensor data from at least one sensor associated with an Atmospheric Water Generator (AWG). Further, in some embodiments, the at least one sensor may be configured for sensing an environment (i.e. surrounding atmosphere) of the AWG. Further, in some embodiments, the at least one sensor may be configured for sensing an interior region of the AWG. Further, in some embodiments, the at least one sensor may be configured for sensing an operational state of at least one component of the AWG. Further, in some embodiments, the at least one sensor may be configured for sensing a characteristic of at least one of an input substance (e.g. air), an intermediate substance and an output substance (e.g. water, by-products etc.) of the AWG. Further, the at least one sensor may be configured for sensing at least one characteristic of an environment of the AWG. Further, in some embodiments, the method may further include a water filter configured for filtering water generated by the AWG. Further, the water filter may be configured for controlling mineral content of the water. Further, the at least one characteristic may correspond to the water. Further, in some embodiments, the at least one sensor may be configured for sensing one or more of a chemical substance and a biological substance in the water.

Further, at 304, the method 300 may include analyzing, using a processing device, the sensor data.

Further, at 306, the method 300 may include determining, using the processing device, a quality parameter associated with the environment based on the analyzing.

Further, at 308, the method 300 may include generating, using the communication device, at least one operational parameter based on the quality parameter. Further, in some embodiments, the at least one operational parameter corresponds to the water filter.

Further, at 310, the method 300 may include transmitting, using the communication device, the at least one operational parameter to at least one regulator configured for controlling the at least one characteristic of the environment based on the at least one operational parameter. Further, in some embodiments, the at least one regulator may include an environment regulator, an input air regulator, a condensation region regulator, a water output regulator and so on. Further, in some embodiments, the at least one characteristic of the environment may include a quantitative indication of one or more of temperature, pressure, humidity, pollutant and microorganism. Further, in some embodiments, the at least one regulator may include at least one air filter configured for filtering air of the environment. Further, in some embodiments, the at least one air filter may include a High efficiency particulate air (HEPA) filter. Further, the at least one operational parameter corresponds to a flow rate and a resistance level associated with the HEPA filter. Further, in some embodiments, the at least one regulator may include an Ultra-Violet (UV) emitter configured for emitting UV radiation into the environment in order to sterilize the environment. Further, in some embodiments, the environment may include an air surrounding the AWG. Further, the AWG may include a condensation region in fluid communication with the air. Further, the UV emitter may be configured for emitting UV radiation into one or more of the air surrounding the AWG and the condensation region.

Figure 4:
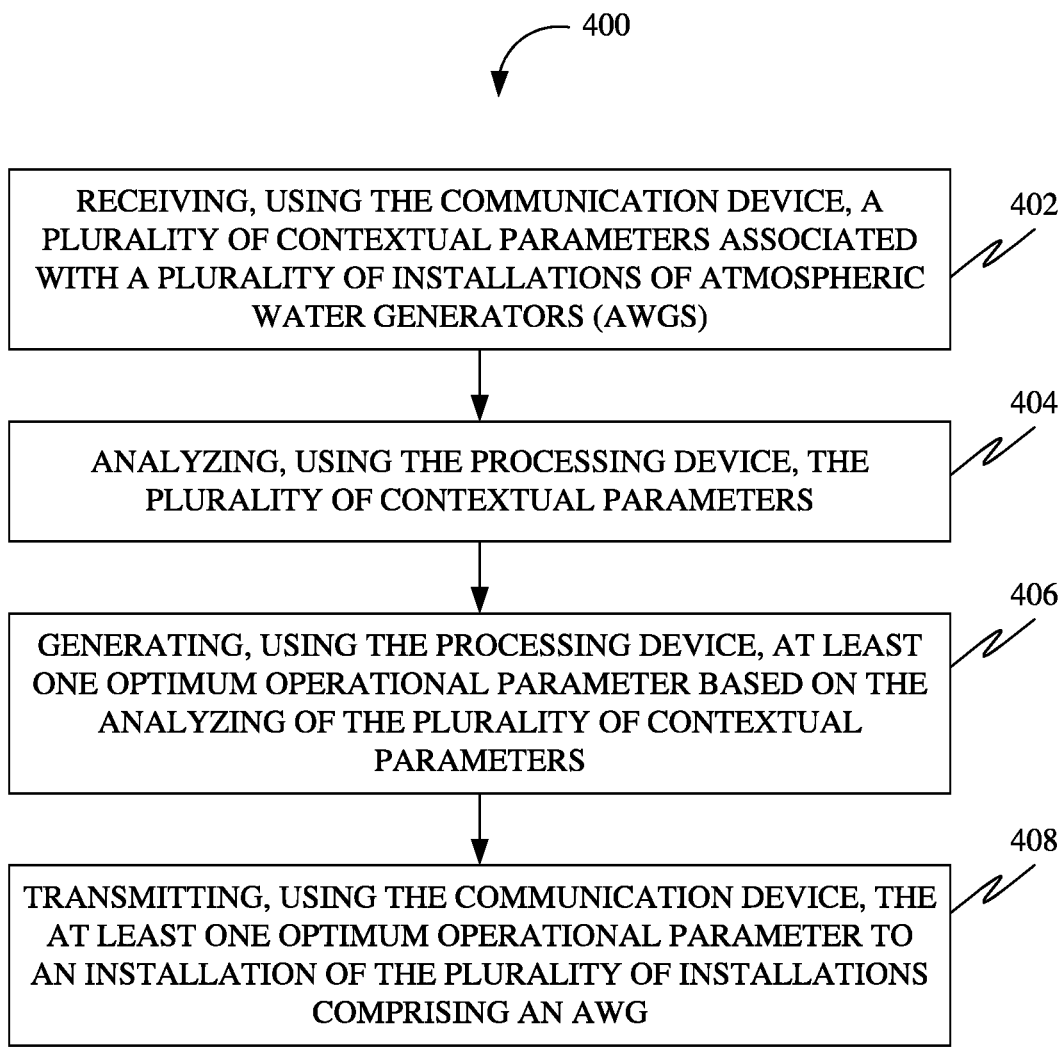
FIG. 4 is a flowchart of a method to facilitate providing at least one optimum operational parameter, in accordance with some embodiments.

FIG. 4 is a flowchart of a method 400 to facilitate providing at least one optimum operational parameter, in accordance with some embodiments. Accordingly, at 402, the method 400 may include receiving, using the communication device, a plurality of contextual parameters associated with a plurality of installations of Atmospheric Water generators (AWGs).

Further, at 404, the method 400 may include analyzing, using the processing device, the plurality of contextual parameters.

Further, at 406, the method 400 may include generating, using the processing device, at least one optimum operational parameter based on the analyzing of the plurality of contextual parameters.

Further, at 408, the method 400 may include transmitting, using the communication device, the at least one optimum operational parameter to an installation of the plurality of installations including an AWG. Further, the installation of at least one AWG regulator configured for controlling operation of the AWG may be based on the at least one optimum operational parameter.

Further, in some embodiments, the plurality of contextual parameters associated with the AWG may include a location data corresponding to a location of the AWG. Further, the method 400 may include retrieving, using a storage device, regulation data associated with operation of AWGs based on the location data. Further, the generating of the at least one optimum parameter may be further based on the regulation data.

Figure 5:
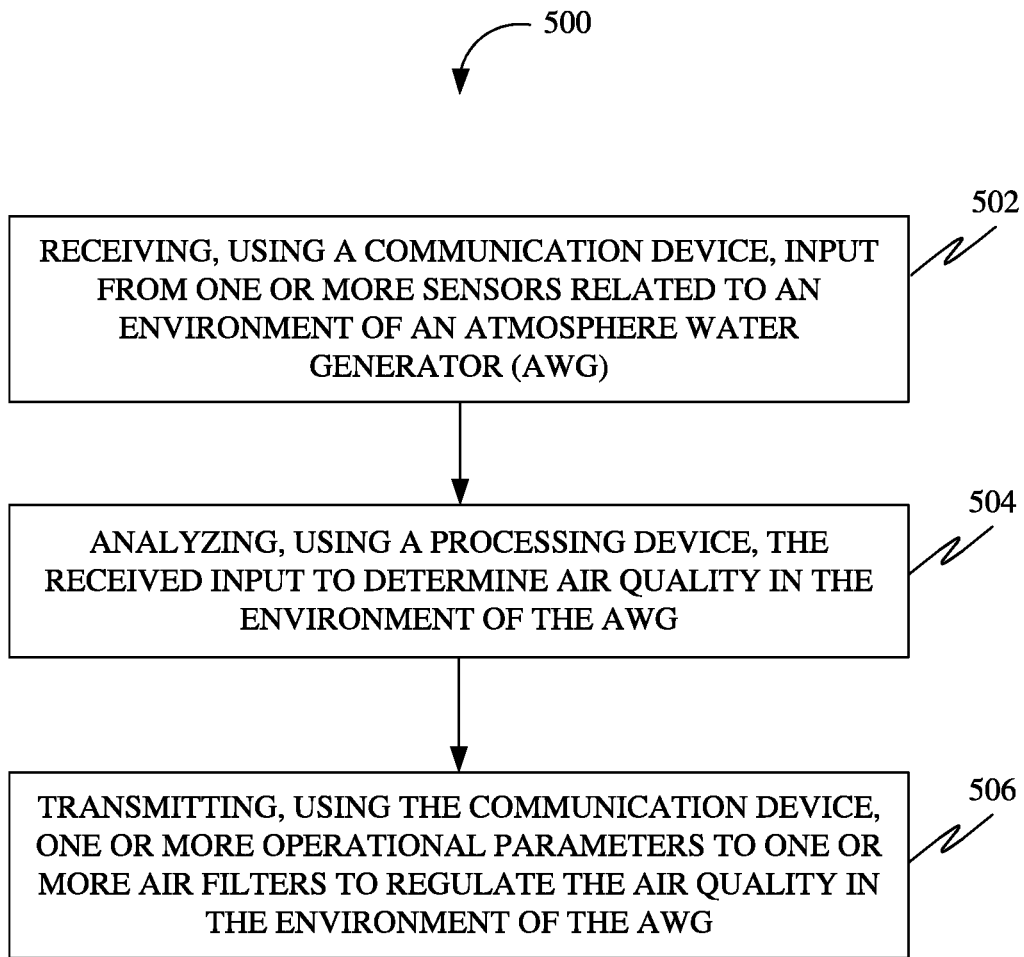
FIG. 5 shows a flowchart of a method to facilitate regulation of an environment of an atmospheric water generator, in accordance with some embodiments.

FIG. 5 shows a flowchart of a method 500 to facilitate regulation of an environment of an atmospheric water generator, in accordance with some embodiments. Accordingly, at 502, the method 500 may include receiving, using a communication device, input from one or more sensors related to an environment of an Atmosphere Water Generator (AWG). For instance, the one or more sensors may include one or more air quality monitors. Accordingly, the one or more sensors may be configured to monitor parameters corresponding to air quality of the environment of the AWG. For instance, the one or more sensors may be configured to monitor particulate matter (PM) concentrations in the air and may be designed to aid in indoor air quality (IAQ) assessments. Further, in an instance, the one or more sensors may be configured to measure CO2, fine dust, temperature and relative humidity in the air. Further, in yet another instance, the one or more sensors may be configured to measure total volatile organic compound, and formaldehyde levels in the air.

Further, at 504, the method 500 may include analyzing, using a processing device, the received input to determine air quality in the environment of the AWG. The received input, including the one or more parameters, received from the one or more sensors including particulate matter (PM) concentrations in the air, CO2, fine dust, temperature and relative humidity, total volatile organic compound, and formaldehyde levels in the air may be analyzed. Further, to determine air quality in the environment of the AWG, all of the parameters may be combined into a comprehensive score describing the air quality in the environment of the AWG. Further, the analysis may include a comparison of the comprehensive score against one or more pre-set levels describing the air quality of the environment of the AWG. Further, the analysis may include analysis of the individual parameters and determining whether each parameter may be below, or above a pre-defined safety limit.

Further, at 506, the method 500 may include transmitting, using the communication device, one or more operational parameters to one or more air filters to regulate the air quality in the environment of the AWG. The one or more operational parameters may describe and control the working of one or more air filtration machines, which may aid in the regulation of the quality of air in the environment of the AWG. For instance, the operational parameters may correspond to working of High Efficiency Particulate Air (HEPA), which may eliminate particulates present in the air up to the size of 0.3 microns, carbon air filters that may make use of activated carbon to neutralize and/or absorb elements such as chemicals and gases, ionic air filters, UV air filters and so on. Further, the operational parameters may regulate the working time and frequency of the one or more air filters. For instance, if the amount of total volatile organic compound and formaldehyde in the air is below a certain pre-defined limit, the operational parameters may reduce the operational time of one or more carbon air filters.

Figure 6:
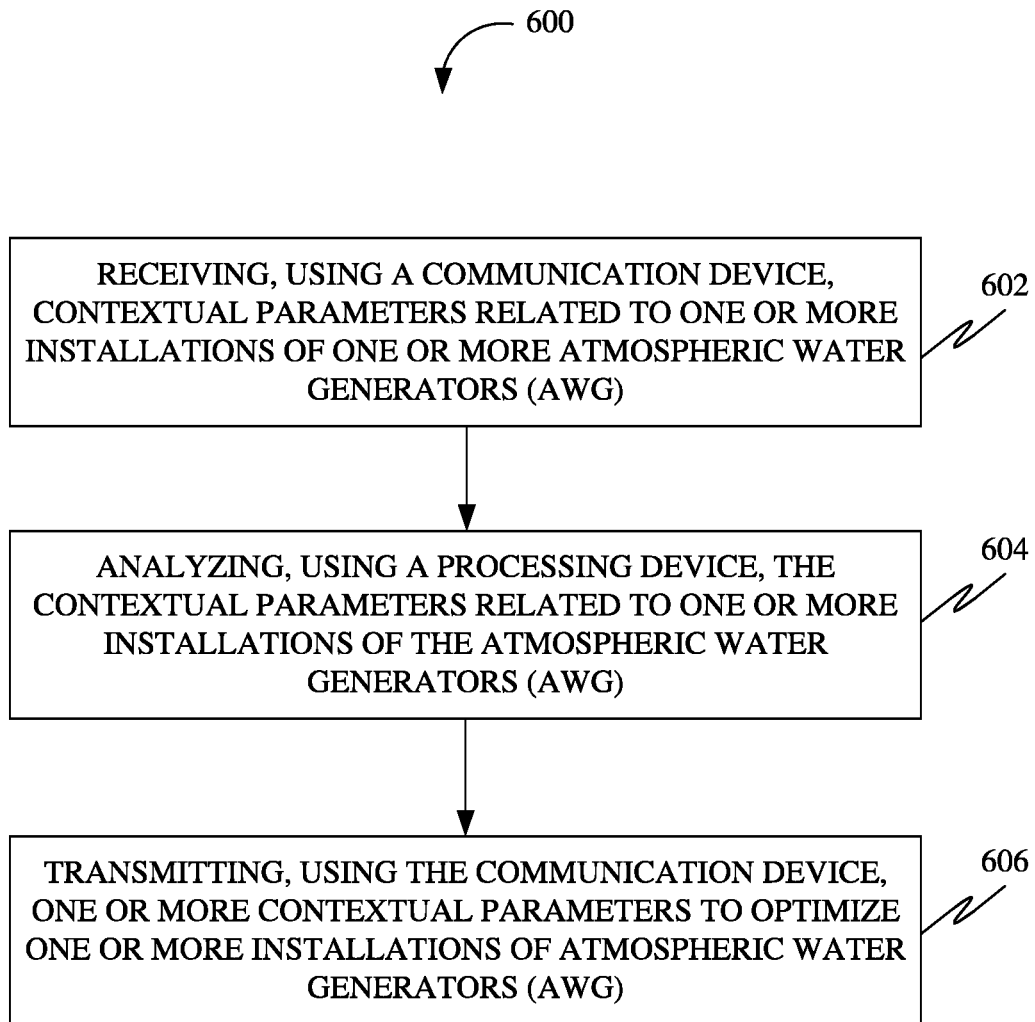
FIG. 6 shows a flowchart of a method to facilitate regulation of working of an atmospheric water generator based on contextual parameters, in accordance with some embodiments.

FIG. 6 shows a flowchart of a method 600 to facilitate regulation of working of an atmospheric water generator based on contextual parameters, in accordance with some embodiments. Accordingly, at 602, the method 600 may include receiving, using a communication device, contextual parameters related to one or more installations of one or more atmospheric water generators (AWG). The one or more contextual parameters may include environmental parameters such as locations of the one or more installations, the average temperature at the location during one or more times, average relative humidity at the location during one or more times, and so on. Further, the contextual parameters may include technical specifications related to the one or more installations, such as details about one or more units of AWGs installed, one or more types of air and water filters included in the one or more AWGs, and so on. Further, the contextual parameters may include one or more operational parameters of the one or more AWGs, such as a time of operation, and additional details such as working of one or more components in the one or more AWGs, such as one or more air and/or water filters.

Further, at 604, the method 600 may include analyzing, using a processing device, the contextual parameters related to one or more installations of the atmospheric water generators (AWGs). The analyzing may include identifying a relationship between the one or more environmental parameters, technical specifications, and operational parameters included in the contextual parameters corresponding to the one or more AWGs. The one or more environmental parameters, such as air quality, temperature, humidity, location, and so on may lead to the installation of AWGs with a particular set of technical specifications, which may operate in accordance with certain fixed operational parameters. For instance, environmental parameters may describe an AWG installed in a location with high relative humidity, and poor air quality such as including a high concentration of total volatile organic compounds, and particulate matter (PM) 2.5 concentrations. Accordingly, the AWG may include one or more carbon filters, and HEPA filters to filter input air. Further, operational parameters related to the AWG may describe an operational intensity of the one or more filters.

Further, at 606, the method 600 may include transmitting, using the communication device, one or more contextual parameters to optimize one or more installations of atmospheric water generators (AWGs). For instance, based on one or more environmental factors of an installation of an AWG, the operational parameters of the AWG may be modified to optimize the generation of water from the AWG. For instance, if the environmental parameters describe an AWG to be installed in a location with high relative humidity, and poor air quality such as including a high concentration of total volatile organic compounds, and particulate matter (PM) 2.5 concentrations, and a high content of microbes such as bacteria, operational parameters related to the AWG may be modified to increase an operational intensity of one or more air filters in the AWG, including one or more HEPA filters, carbon filters, and so on. Further, after condensation of water through the AWG, the operational parameters may dictate the working of a UV filter to reduce microbial level in the water.

Figure 7:
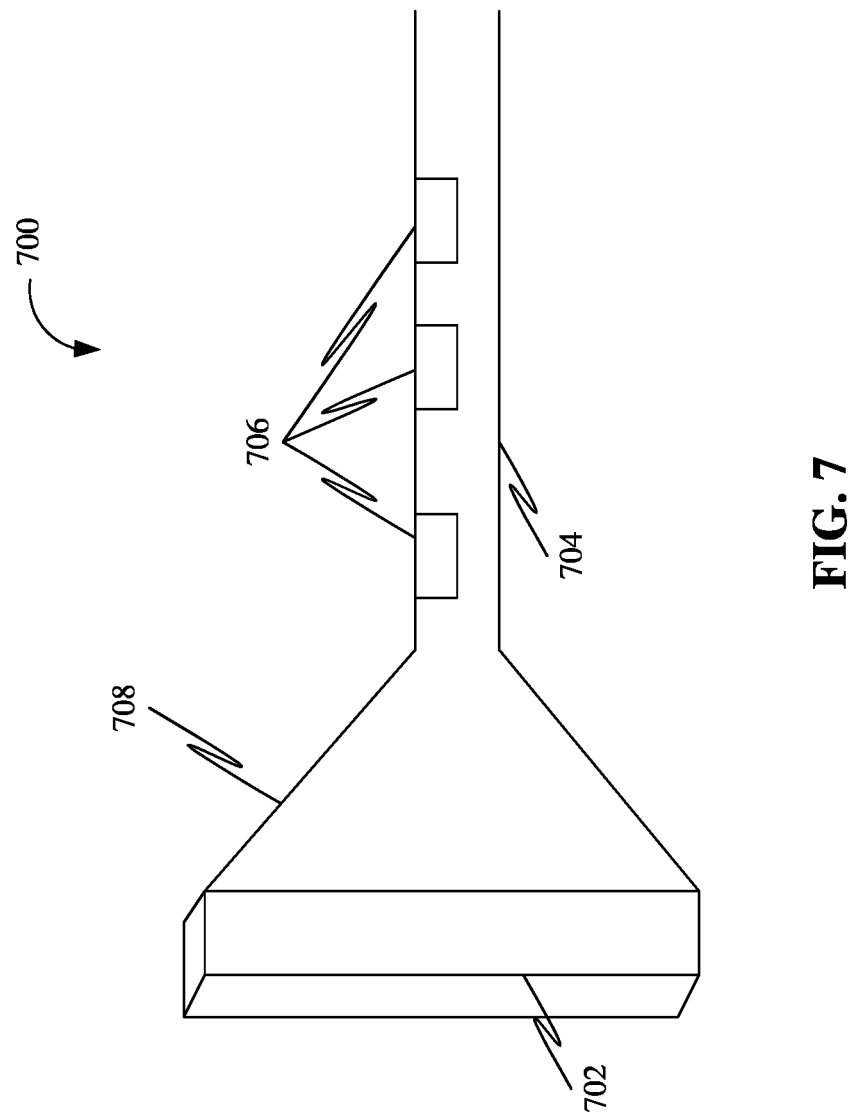
FIG. 7 shows a block diagram of an air filtration unit connected to an AWG, in accordance with some embodiments.

FIG. 7 shows a block diagram of an air filtration unit 700 connected to an AWG, in accordance with some embodiments. Further, air filtration unit 700 may filter air inside an environment of the AWG. Accordingly, the air filtration unit 700 may include Afpro® bag filters or similar filters. Further, the air filtration unit 700 may include HEPA air filters 702 to impede microorganism growth, such as bacterial or fungal, and for removal of particles. Further, the filtered air may be collected into a collection chamber 708, and may be passed through a sterilization tube 704. Further, the sterilization tube 704 may include one or more UV lights 706 before the air reaches a condensation area of the AWG machine.

Figure 8:
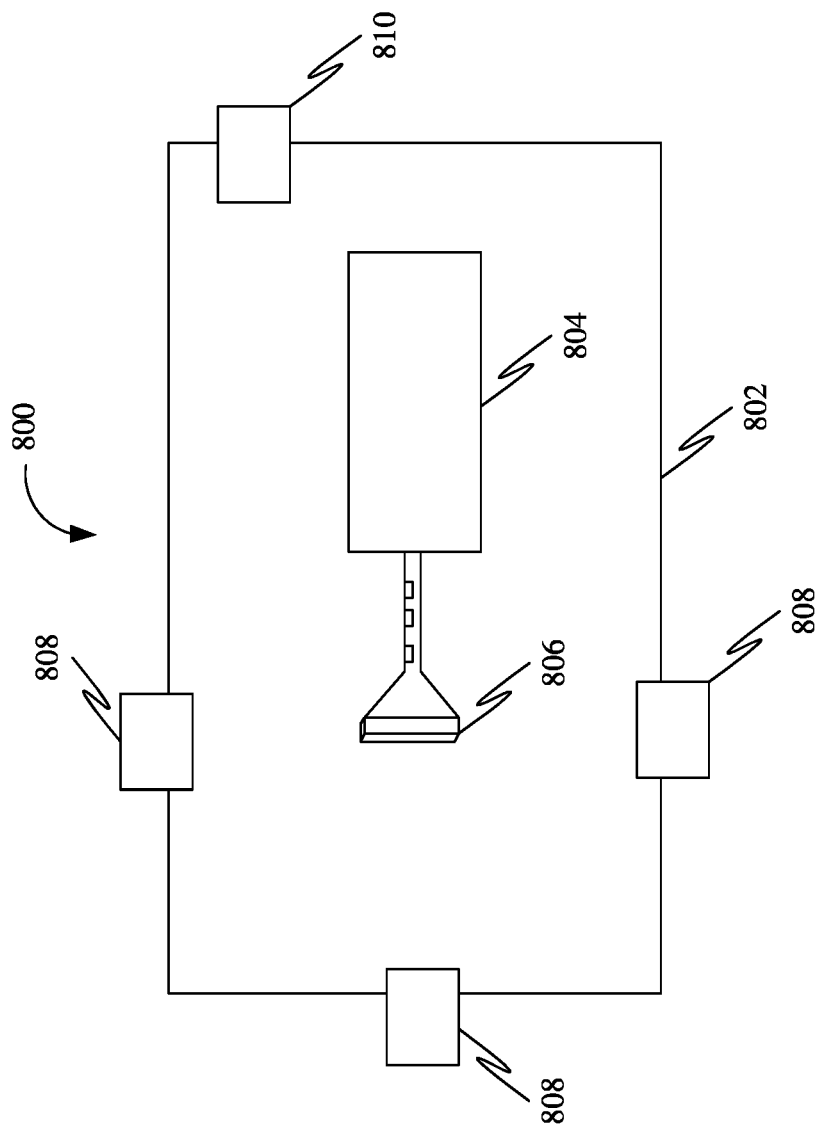
FIG. 8 shows a process of air management, in accordance with some embodiments.

FIG. 8 shows a process 800 of air management, in accordance with some embodiments. Air may be controlled and filtered through one or more primary air filtration units 808 as the air enters an environment 802 where an AWG 804 may be placed. Further, the air may be controlled and filtered using a secondary air filtration unit 806 before the air enters a condensation area in the AWG 804. Further, air may be pumped out to a room through an air output unit 810

Figure 9:
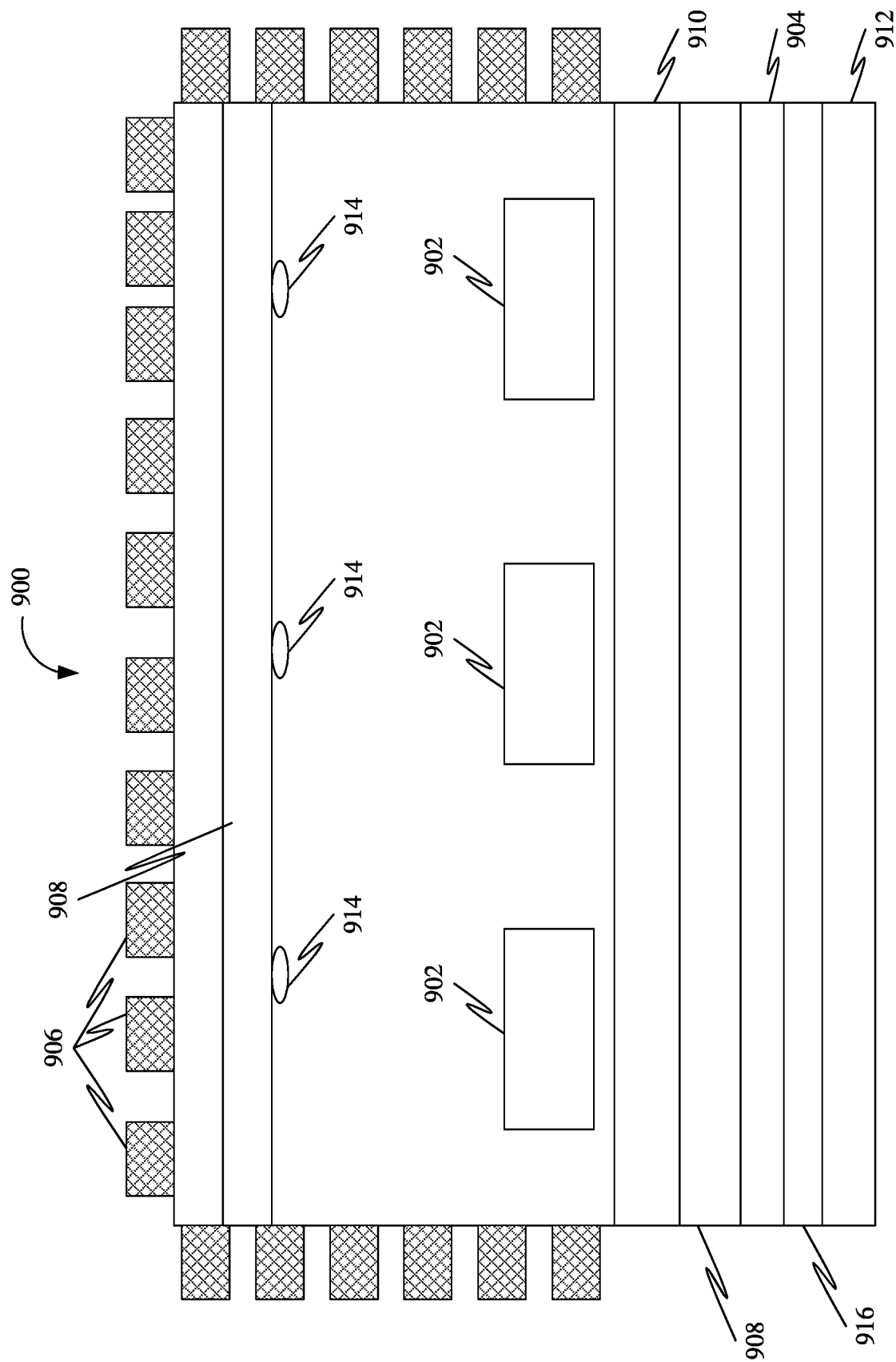
FIG. 9 shows an exemplary layout of a water generation plant in accordance with some embodiments.

FIG. 9 shows an exemplary layout of a water generation plant 900 in accordance with some embodiments. Accordingly, the water generation plant 900 may include a horizontal layout to allow air to spread better in the horizontal layout, and lead to better water generation. Moist air may be sucked in using one or more air vacuum machines 904 from outside and air may then enter the water generation plant 900 from a lower end (near ground) to spread all over the water generation plant 900. Dry air may exit from the top of the water generation plant 900 as dry air is lighter than the moist air. Further, the water generation plant 900 may include an outdoor dust suppression barrier system 916 surrounding water generation plant 900, to be used in case of dusty and windy weather to capture dust and particles and to optimize working of the one or more air vacuum machines 904. Further, the water generation plant 900 may include one or more AWGs 902, the space between which may be at least 131.234 feet (40 m), and a vertical space of 393.701 feet (120 m). Further, in an embodiment, the water generation plant 900 may have a vertical layout, so as to save cost. Further, the water generation plant 900 may include a plurality of solar panels 906 surrounding the water generation plant 900 to be able to generate power, and to follow the sun's directions (like a clock). Further, the water generation plant 900 may include an air pre-filtration system 908 (including one or more UV lights) at the bottom and at the top of the water generation plant 900. Further, upon installation of the air pre-filtration system 908 in the water generation plant 900, in order to protect one or more workers of the water generation plant 900 from damage of the one or more UV lights, the one or more UV lights may be isolated in a separate area. Further, the one or more UV lights may automatically turn off in the presence of a worker, which may be determined using one or more sensors, such as motion sensors. Further, the AWG plant may be environment friendly and green.

Exterior and interior thermostats to control temperature and humidity in the air may be included in the water generation plant 900. Further, both exterior and interior thermostats may send information to a computing device which may adjust the temperature and humidity in the air inside the water generation plant 900 to a desired level, such as at 77 F and 80% humidity. In an instance, the temperature inside the water generation plant 900 may be controlled by an air cooling and heating system 910. Further, the water generation plant 900 may include a storage tank 912 for water shortage and for shortage of humidity. The storage tank may cover up shortage of water production in case of a disabled AWG of the one or more AWGs 902 and in case of shortage of humidity. Further, the water generation plant 900 may include one or more water sprinklers 914 to increase humidity in case of shortage of humidity in the air. The water generation plant 900 may be set up in an area where humidity in the air may remain high all year around such as for example Eureka, Calif. For instance, if the humidity lowers down to 50%, the one or more sprinklers 914 may use water inside the storage tank, and sprinkle/spray water in the water generation plant 900 to increase the humidity to a desired level. For instance, if temperature outside the AWG plant is 40 F the AWG plant may be heated to increase the temperature to 77 F. However, this may lead to a decrease in humidity level. Accordingly, if the loss in humidity is 30%, appropriate amount of water may be sprinkled/sprayed to increase the humidity. Further, the water generation plant 900 may be designed with sound proofing materials (floors, ceilings, walls, the entire structure may of the water generation plant 900 may be isolated with isolation systems). Further, the water generation plant 900 may be built as large as possible to allow air to enter and exit in easy way through advance sucking moist air and pushing out dry air through air vacuum, and pumping systems. Further, water generation plant 900 plant may be built with green materials, so as to remain environment friendly, and may include the one or more AWGs 902 designed to filter water with long lasting filters such as pre carbon filtration, post carbon filtration, reverse osmosis, TCR carbon, and so on. Further, the UV exposure in the water generation plant 900 may extend life of the one or more filters. Further, the solar panels 906 in all directions may produce 4000 KW of electricity per day to allow the one or more AWGs 902 to produce 20,000 liters of water per day, Further, the water generation plant 900 may include an electrical control room, a temperature and humidity control system, a water testing lab for water quality control, biological control and air quality control, and a bottling process plant. After biological water testing for water quality control, biological control and air quality control, minerals may be added to the water, such as in accordance with local laws and regulations.

Figure 10:
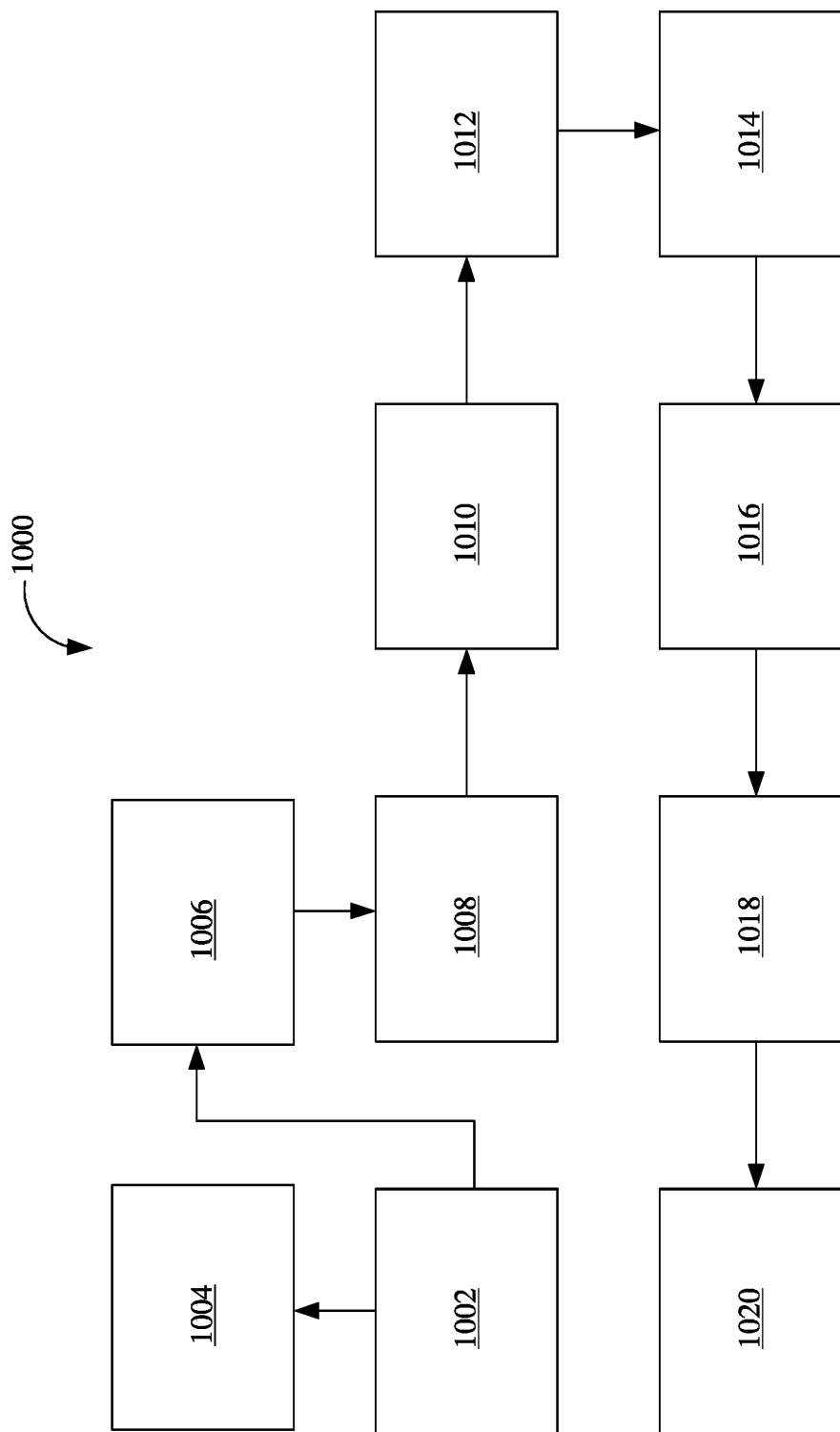
FIG. 10 shows an exemplary process of generation of water using an AWG, in accordance with some embodiments.

FIG. 10 shows an exemplary process 1000 of generation of water using an AWG, in accordance with some embodiments. Accordingly, upon generation of water using one or more AWGs in an AWG plant at 1002, the generated water may be sent to a reservoir for storage at 1004. Further, at 1006, the generated water may undergo UV exposure to kill bacteria, and other microbes. Further, one or more water filters may be used to control mineral content in water generated by the AWG. After UV exposure, the water may pass through multiple stages of filtration, namely pre-carbon at 1008, post-carbon at 1010, reverse osmosis membrane at 1012, and TCR carbon at 1014, followed by further exposure to UV lights at at 1016. Further, minerals may be added to the water at 1018, such as in accordance with local laws and regulations, upon which, pure drinking water may be obtained at 1020.

Figure 11:
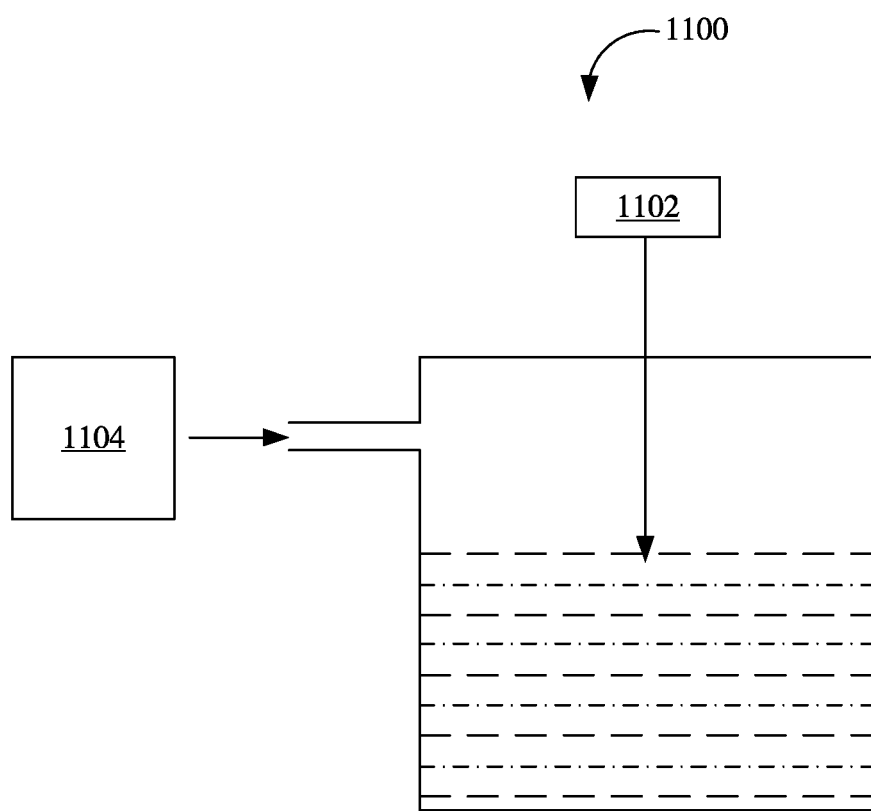
FIG. 11 shows an exemplary mineral addition tank, in accordance with some embodiments.

FIG. 11 shows an exemplary mineral addition tank 1100, in accordance with some embodiments. Water from an AWG 1104 may be collected into the mineral addition tank 1100. Further, the mineral addition tank may be marked with one or more volume indicator markings to indicate a volume of water in the mineral addition tank 1100. Further, electrolyte blends or minerals 1102 may be added to the water in the mineral addition tank 1100. Further, an amount of electrolyte blends or minerals 1102 may be fixed corresponding to the volume of water in the mineral addition tank.

Figure 12:
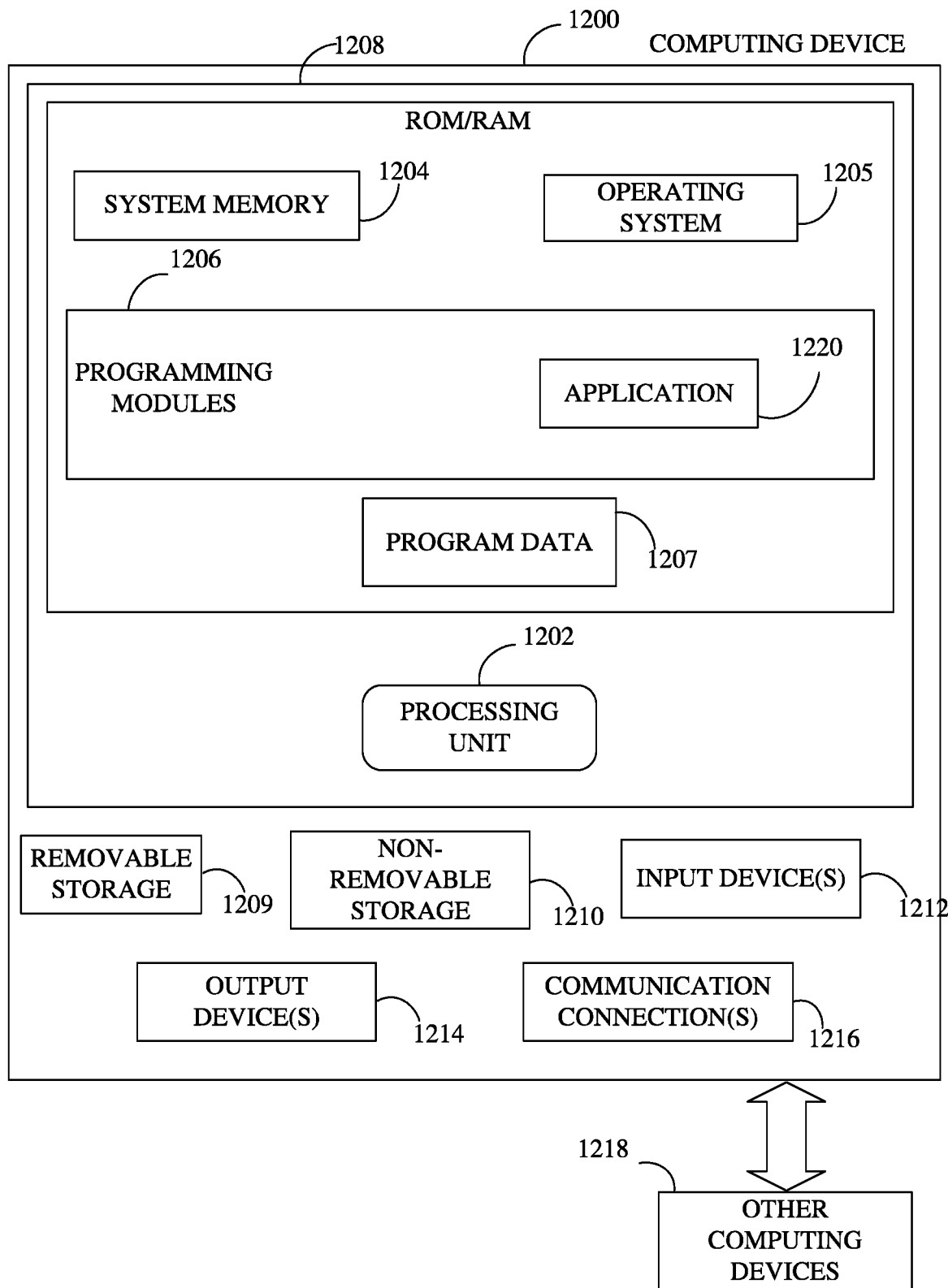
FIG. 12 is a block diagram of a computing device for implementing the methods disclosed herein, in accordance with some embodiments.

With reference to FIG. 12, a system consistent with an embodiment of the disclosure may include a computing device or cloud service, such as computing device 1200. In a basic configuration, computing device 1200 may include at least one processing unit 1202 and a system memory 1204.

Depending on the configuration and type of computing device, system memory 1204 may comprise, but is not limited to, volatile (e.g. random-access memory (RAM)), non-volatile (e.g. read-only memory (ROM)), flash memory, or any combination. System memory 1204 may include operating system 1205, one or more programming modules 1206, and may include a program data 1207. Operating system 1205, for example, may be suitable for controlling computing device 1200's operation. In one embodiment, programming modules 1206 may include machine learning module. Furthermore, embodiments of the disclosure may be practiced in conjunction with a graphics library, other operating systems, or any other application program and is not limited to any particular application or system. This basic configuration is illustrated in FIG. 12 by those components within a dashed line 1208.

Computing device 1200 may have additional features or functionality. For example, computing device 1200 may also include additional data storage devices (removable and/or non-removable) such as, for example, magnetic disks, optical disks, or tape. Such additional storage is illustrated in FIG. 12 by a removable storage 1209 and a non-removable storage 1210. Computer storage media may include volatile and nonvolatile, removable and non-removable media implemented in any method or technology for storage of information, such as computer-readable instructions, data structures, program modules, or other data. System memory 1204, removable storage 1209, and non-removable storage 1210 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1200. Any such computer storage media may be part of device 1200. Computing device 1200 may also have input device(s) 1212 such as a keyboard, a mouse, a pen, a sound input device, a touch input device, a location sensor, a camera, a biometric sensor, etc. Output device(s) 1214 such as a display, speakers, a printer, etc. may also be included. The aforementioned devices are examples and others may be used.

Computing device 1200 may also contain a communication connection 1216 that may allow device 1200 to communicate with other computing devices 1218, such as over a network in a distributed computing environment, for example, an intranet or the Internet. Communication connection 1216 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1204, including operating system 1205. While executing on processing unit 1202, programming modules 1206 (e.g., application 1220 such as a media player) may perform processes including, for example, one or more stages of methods, algorithms, systems, applications, servers, databases as described above. The aforementioned process is an example, and processing unit 1202 may perform other processes. Other programming modules that may be used in accordance with embodiments of the present disclosure may include machine learning application etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the disclosure has been explained in relation to its preferred embodiment, it is to be understood that many other possible modifications and variations can be made without departing from the spirit and scope of the disclosure.

What is claimed is:

1. A method of facilitating atmospheric water generation comprising:
    receiving, using a communication device, sensor data from at least one sensor associated with an Atmospheric Water Generator (AWG), wherein the at least one sensor is configured for sensing at least one characteristic of an environment of the AWG;
    analyzing, using a processing device, the sensor data;
    generating, using the communication device, at least one operational parameter based on the analyzing;
    transmitting, using the communication device, the at least one operational parameter to at least one regulator; and
    controlling, using the at least one regulator, the at least one characteristic of the environment based on the at least one operational parameter;
    wherein the at least one regulator comprises at least one air filter configured for filtering air of the environment and an Ultra-Violet (UV) emitter configured for emitting UV radiation into the environment in order to sterilize the environment, wherein the at least one air filter comprises a High efficiency particulate air (HEPA) filter, wherein the at least one operational parameter corresponds to a flow rate and a resistance level associated with the HEPA filter, wherein the environment comprises an air surrounding the AWG, wherein the UV emitter is configured for emitting the UV radiation into the air surrounding the AWG, wherein the processing device is a microprocessor.

2. The method of claim 1, wherein the at least one characteristic of the environment comprises a quantitative indication of at least one of temperature, pressure, humidity, pollutant and microorganism.

3. The method of claim 1, wherein the AWG comprises a condensation region in fluid communication with the air, wherein the UV emitter is configured for emitting UV radiation into the condensation region.

4. The method of claim 1 further comprising a water filter configured for filtering water generated by the AWG, wherein the water filter is configured for controlling mineral content of the water, wherein the at least one characteristic corresponds to the water, wherein the at least one operational parameter corresponds to the water filter.

5. The method of claim 1, wherein the at least one sensor is configured for sensing at least one of a chemical substance and a biological substance in the water.

6. The method of claim 1 comprising:
    receiving, using the communication device, a plurality of contextual parameters associated with a plurality of installations of Atmospheric Water generators (AWGs);
    analyzing, using the processing device, the plurality of contextual parameters;
    generating, using the processing device, at least one optimum operational parameter based on the analyzing of the plurality of contextual parameters;
    transmitting, using the communication device, the at least one optimum operational parameter to an installation of the plurality of installations comprising an AWG, wherein the installation of at least one AWG regulator configured for controlling operation of the AWG is based on the at least one optimum operational parameter;
    storing, using a storage device, the at least one optimum operational parameter in association with indication of corresponding plurality of contextual parameters, wherein the plurality of contextual parameters associated with the AWG comprises a location of the AWG;
    retrieving, using the storage device, a regulation associated with operation of AWGs based on the location, wherein the generating of the at least one optimum parameter is further based on the regulation; and
    wherein the storage device is a RAM, a ROM, an electrically erasable read-only memory (EEPROM), a flash memory, a CD-ROM, a digital versatile disk (DVD), a magnetic cassette, a magnetic tape or a magnetic disk, wherein the at least one optimum operational parameter corresponds to an optimum flow rate and an optimum resistance level associated with the HEPA filter.

* * * * *